United States Patent
Keene et al.

(10) Patent No.: US 11,759,333 B2
(45) Date of Patent: Sep. 19, 2023

(54) SPINAL IMPLANT SYSTEM AND METHODS OF USE

(71) Applicant: Warsaw Orthopedic, Inc., Warsaw, IN (US)

(72) Inventors: Patrick Keene, Memphis, TN (US); Darren L Davis, Arlington, TN (US); John Andrew Hall, Germantown, TN (US)

( * ) Notice: Subject to any disclaimer, the term of this patent is extended or adjusted under 35 U.S.C. 154(b) by 26 days.

(21) Appl. No.: 16/599,580

(22) Filed: Oct. 11, 2019

(65) Prior Publication Data

US 2021/0106436 A1     Apr. 15, 2021

(51) Int. Cl.
| A61B 17/70 | (2006.01) |
| A61F 2/44 | (2006.01) |
| A61F 2/46 | (2006.01) |
| A61B 17/80 | (2006.01) |
| A61F 2/28 | (2006.01) |

(52) U.S. Cl.
CPC ........ *A61F 2/4611* (2013.01); *A61B 17/7071* (2013.01); *A61B 17/808* (2013.01); *A61F 2/44* (2013.01); *A61F 2002/2835* (2013.01); *A61F 2002/4627* (2013.01); *A61F 2220/0025* (2013.01); *A61F 2310/00023* (2013.01)

(58) Field of Classification Search
CPC ............ A61F 2/4611; A61F 2002/2835; A61F 2002/4627; A61F 2/44; A61F 2220/0025; A61F 2310/00023; A61F 2/4455; A61B 17/7071; A61B 17/808
See application file for complete search history.

(56) References Cited

U.S. PATENT DOCUMENTS

| 7,727,235 | B2 | | 6/2010 | Contiliano et al. |
| 8,303,631 | B2 | * | 11/2012 | Duggal .............. A61B 17/7071 |
| | | | | 606/250 |
| 8,535,356 | B2 | * | 9/2013 | Kirschman ........ A61B 17/8052 |
| | | | | 606/291 |
| 9,314,274 | B2 | * | 4/2016 | Amstutz ............ A61B 17/7091 |
| 9,730,802 | B1 | * | 8/2017 | Harvey ................ A61F 2/4611 |
| D801,796 | S | * | 11/2017 | Sweeney ........................ D8/387 |
| D831,475 | S | * | 10/2018 | Sweeney ........................ D8/387 |
| D831,476 | S | * | 10/2018 | Sweeney ........................ D8/387 |
| 10,299,839 | B2 | * | 5/2019 | Sicvol ................ A61B 17/7035 |
| 2007/0274800 | A1 | * | 11/2007 | Mikkonen ............ A61B 17/862 |
| | | | | 411/15 |

(Continued)

FOREIGN PATENT DOCUMENTS

JP         11070126 A         3/1999

OTHER PUBLICATIONS

ISA/KR Korean Intellectual Property Office, Republic or Korea, International application No. PCT/US2020/053786, Written Opinion of the International Searching Authority, International Search Report, dated Jan. 20, 2021.

*Primary Examiner* — Bruce E Snow
(74) *Attorney, Agent, or Firm* — Sorell, Lenna & Schmidt, LLP

(57) ABSTRACT

A spinal implant includes a first member configured to penetrate tissue and a second member. The second member has an abutment engageable with a surgical instrument and at least one peripheral capture element engageable with a moveable arm of the surgical instrument. Systems, spinal constructs, surgical instruments and methods are disclosed.

17 Claims, 8 Drawing Sheets

(56) References Cited

U.S. PATENT DOCUMENTS

| | | |
|---|---|---|
| 2011/0125267 A1* | 5/2011 | Michelson ........... A61B 17/866 623/17.11 |
| 2011/0306984 A1 | 12/2011 | Sasing |
| 2014/0066758 A1* | 3/2014 | Marik ................ A61B 17/7064 600/431 |
| 2014/0358184 A1 | 12/2014 | Varela et al. |
| 2019/0239935 A1* | 8/2019 | Willis .................. A61B 17/866 |
| 2021/0322184 A1* | 10/2021 | Nichols ................ A61F 2/4425 |

* cited by examiner

SPINAL IMPLANT SYSTEM AND METHODS OF USE

TECHNICAL FIELD

The present disclosure generally relates to medical devices for the treatment of musculoskeletal disorders, and more particularly to a surgical system and method for treating a spine.

BACKGROUND

Spinal disorders such as degenerative disc disease, disc herniation, osteoporosis, spondylolisthesis, stenosis, kyphosis, scoliosis and other curvature abnormalities, tumor and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy, laminoplasty and implantable prosthetics. For example, surgical treatment may include lam inoplasty, which can employ implants such as plates and bone fasteners to provide stability to a treated region. These implants can redirect stresses away from a damaged or defective region while healing takes place to restore proper alignment and generally support the vertebral members. During surgical treatment, the plates and bone fasteners can be delivered to a surgical site. Surgical instruments are employed, for example, to engage the fasteners for attaching the plates to the exterior of one or more vertebral members. This disclosure describes an improvement over these prior technologies.

SUMMARY

In one embodiment, a spinal implant is provided. The spinal implant comprises a first member configured to penetrate tissue. A second member includes an abutment engageable with a surgical instrument and at least one peripheral capture element engageable with a moveable arm of the surgical instrument. In some embodiments, systems, spinal constructs, methods and surgical instruments are disclosed.

In one embodiment, a surgical instrument is provided. The surgical instrument comprises a shaft extending between a proximal end and a distal end. The distal end is configured for engagement with an abutment of a spinal implant. An opening is disposed at the distal end and configured for disposal of a portion of the spinal implant. A moveable arm extends along the shaft and is configured to engage at least one peripheral capture element disposed with the spinal implant.

In one embodiment, a spinal implant system is provided. The spinal implant system comprises a spinal implant including a first member configured to penetrate tissue and a second member including an abutment and at least one peripheral capture element. A surgical instrument includes a shaft extending between a proximal end and a distal end. The distal end is configured for engagement with the abutment. An opening is disposed at the distal end and is configured for disposal of a portion of the second member. A moveable arm extends along the shaft and is configured for rotation between a capture orientation engaging the least one peripheral capture element and a release orientation.

BRIEF DESCRIPTION OF THE DRAWINGS

The present disclosure will become more readily apparent from the specific description accompanied by the following drawings, in which.

DETAILED DESCRIPTION

Figure 1:
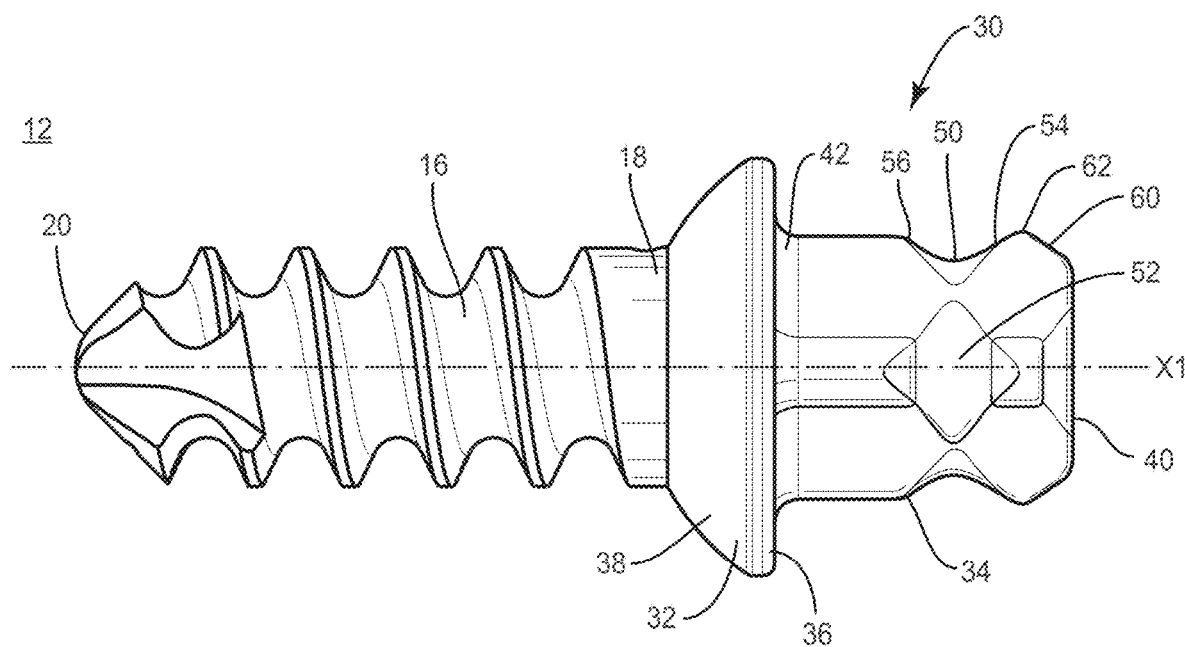
FIG. 1 is a side view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system and a method for treating a spine. In some embodiments, the systems and methods of the present disclosure are employed with a laminoplasty procedure.

In some embodiments, the present surgical system comprises a surgical instrument, for example, a self-retaining screw driver configured for connection with a head of a spinal implant, for example, a bone screw. In some embodiments, the driver is configured to retain the bone screw and resist and/or prevent disengagement during insertion to a surgical site. In some embodiments, the driver is configured to retain the bone screw and resist and/or prevent disengagement from the bone screw during an applied torque for engagement with tissue. In some embodiments, the driver is easily detached from the bone screw after the bone screw is engaged with tissue. In some embodiments, the bone screw is utilized to secure spinal constructs, for example, a laminoplasty plate with patient anatomy.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics.

In some embodiments, the disclosed system may be alternatively employed in a surgical treatment with a patient in a prone or supine position, and/or employ various surgical approaches to the spine, including anterior, posterior, postero mid-line, direct lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including surgical instruments, spinal constructs, implants, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-11, there are illustrated components of a surgical system, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 can be employed, for example, with a minimally invasive procedure, including percutaneous techniques, mini-open and open surgical techniques to manipulate tissue, deliver and introduce instrumentation and/or components of spinal constructs at a surgical site within a body of a patient, for example, a section of a spine. In some embodiments, spinal implant system 10 can be employed, for example, in laminoplasty procedures to treat patients suffering from a spinal disorder to provide stabilization and decompression, as described herein.

Figure 11:
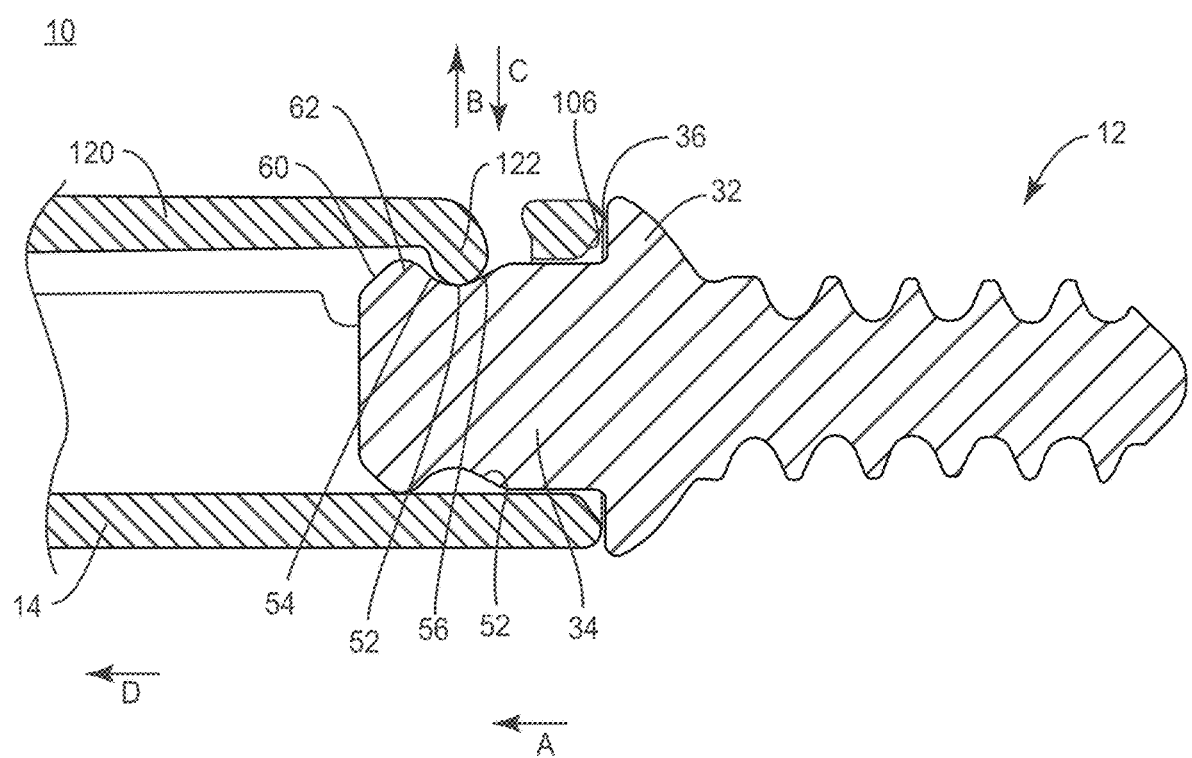
FIG. 11 is a break away cross section view of components of one embodiment of a surgical system in accordance with the principles of the present disclosure.
Figure 12:
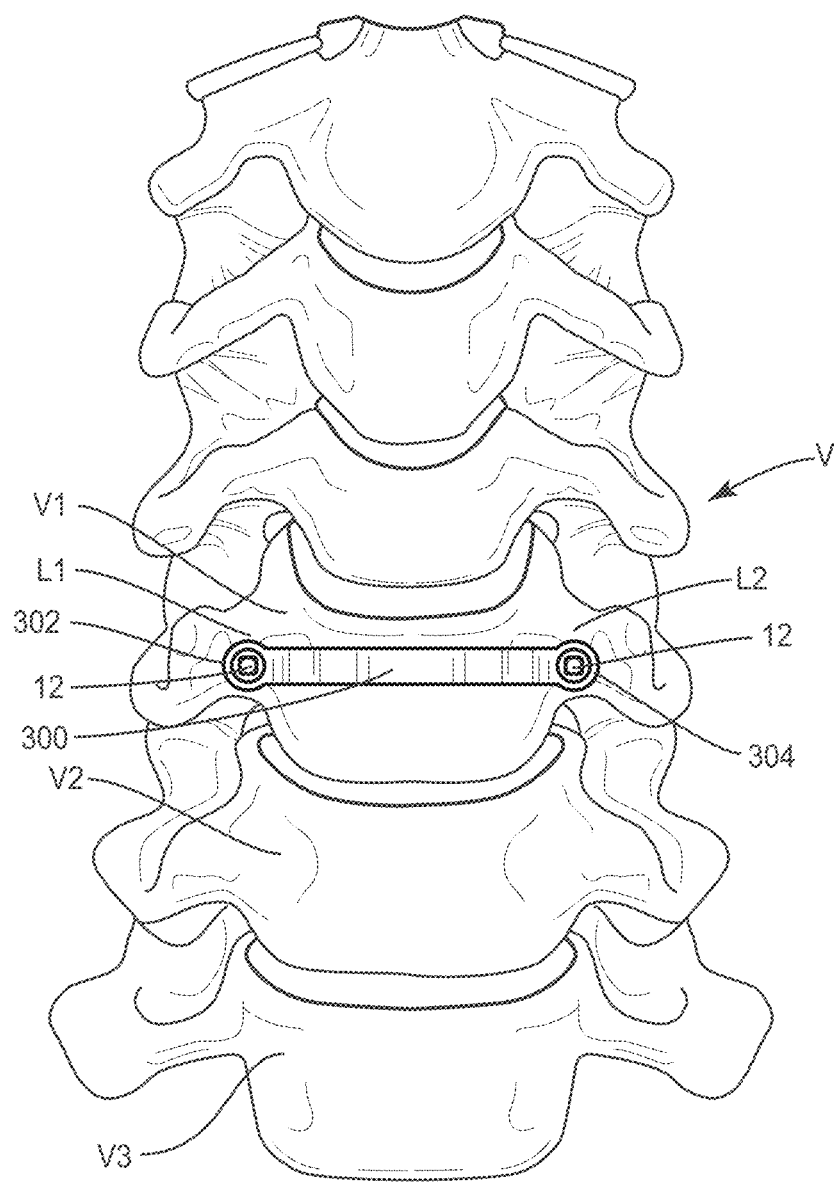
FIG. 12 is a plan view of components of one embodiment of a surgical system in accordance with the principles of the present disclosure disposed with vertebrae.

Spinal implant system 10, as described herein, includes a spinal implant, for example, a bone screw 12 that is engageable with a surgical instrument, for example, a surgical driver 14, as shown in FIGS. 1-11. Surgical driver 14 is configured to retain bone screw 12 during engagement with tissue in a surgical procedure, for example, implant of a lam inoplasty plate 300 (FIG. 12).

Bone screw 12 includes a member, for example, a shaft 16, as shown in FIG. 1. Shaft 16 extends between a proximal end 18 and a distal end 20. Shaft 16 has a cylindrical cross-sectional configuration between ends 18, 20. In some embodiments, a portion of shaft 16 may have alternate cross section configurations, such as, for example, oval, oblong, triangular, square, polygonal, irregular, uniform, non-uniform, offset, staggered, and/or tapered. Shaft 16 defines an axis X1.

Shaft 16 includes a thread form on an outer surface thereof. In some embodiments, the thread form may extend such that shaft 16 is threaded along the entire length thereof. In some embodiments, all or only a portion of shaft 16 may have various surface configurations, such as, for example, rough, threaded, arcuate, undulating, porous, semi-porous, dimpled, polished and/or textured.

Bone screw 12 includes a member 30 that includes an abutment 32 and a head 34. Abutment 32 includes a proximal face 36 and a tapered distal surface 38, as shown in FIG. 1. Surface 38 extends from proximal face 36 to proximal end 18. Proximal face 36 extends transverse, for example, perpendicular to axis X1. In some embodiments, proximal face 36 extends at other angular orientations relative to axis X1, for example, acute or obtuse. Proximal face 36 is configured for a flush engagement with a portion of surgical driver 14, as described herein. Proximal face 36 defines a stop for limiting translation of surgical driver 14 relative to head 34, as described herein. For example, proximal face 36 resists and/or prevents surgical driver 14 from translating past a capture element disposed with head 34 to retain bone screw 12, as described herein.

Figure 3:
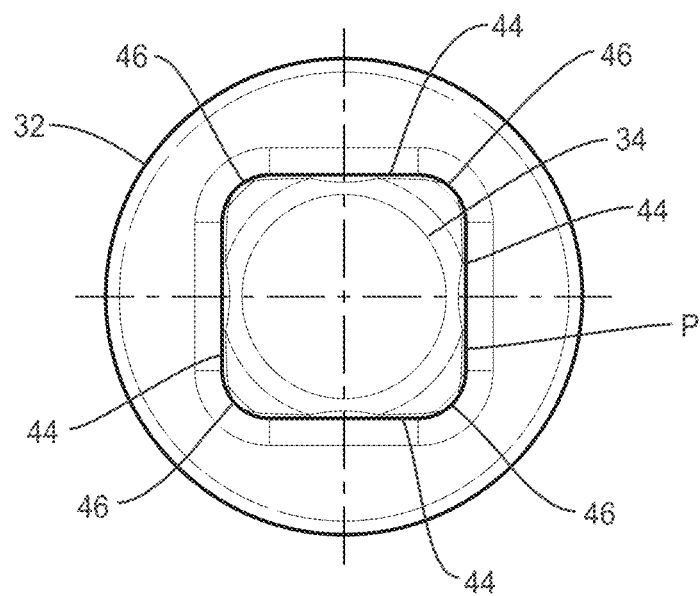
FIG. 3 is an axial view of the components shown in FIG. 1.

Head 34 extends from proximal face 36. In some embodiments, head 34 extends along axis X1 such that head 34 is perpendicular to proximal face 36. In some embodiments, head 34 extends parallel or at other angular orientations relative to proximal face 36, for example, acute or obtuse. Head 34 extends between a proximal end 40 and a distal end 42. Head 34 includes a rectangular cross section configuration having walls 44 that define a perimeter P, as shown in FIG. 3. Walls 44 merge at edges 46. In some embodiments, head 34 may have alternate cross section configurations, such as, for example, oval, oblong, triangular, square, polygonal, irregular, uniform, non-uniform, offset, staggered, and/or tapered.

Figure 2:
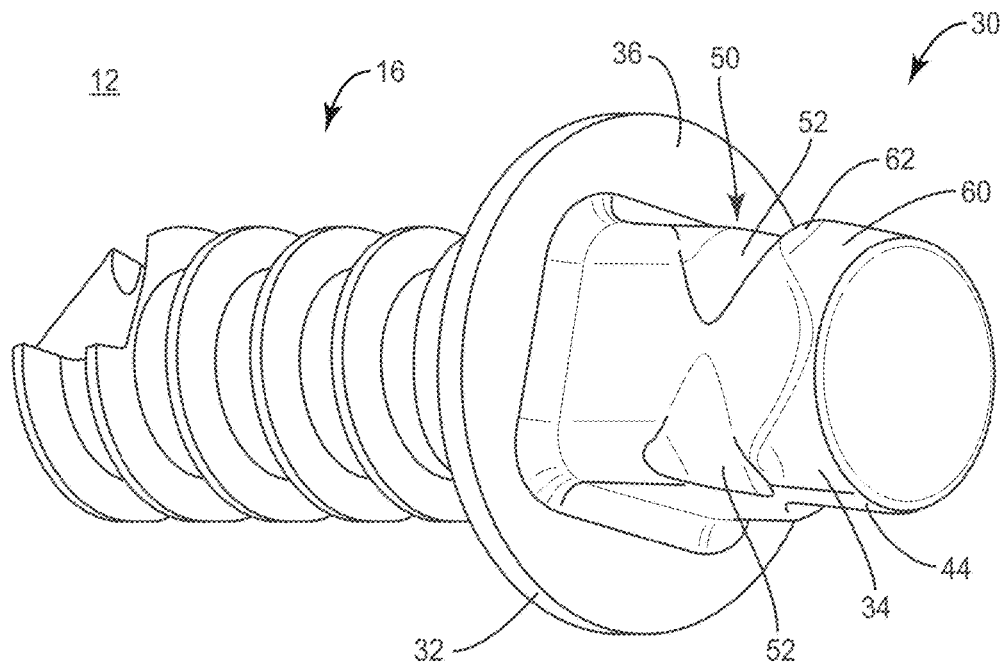
FIG. 2 is a perspective view of the components shown in FIG. 1.
Figure 4:
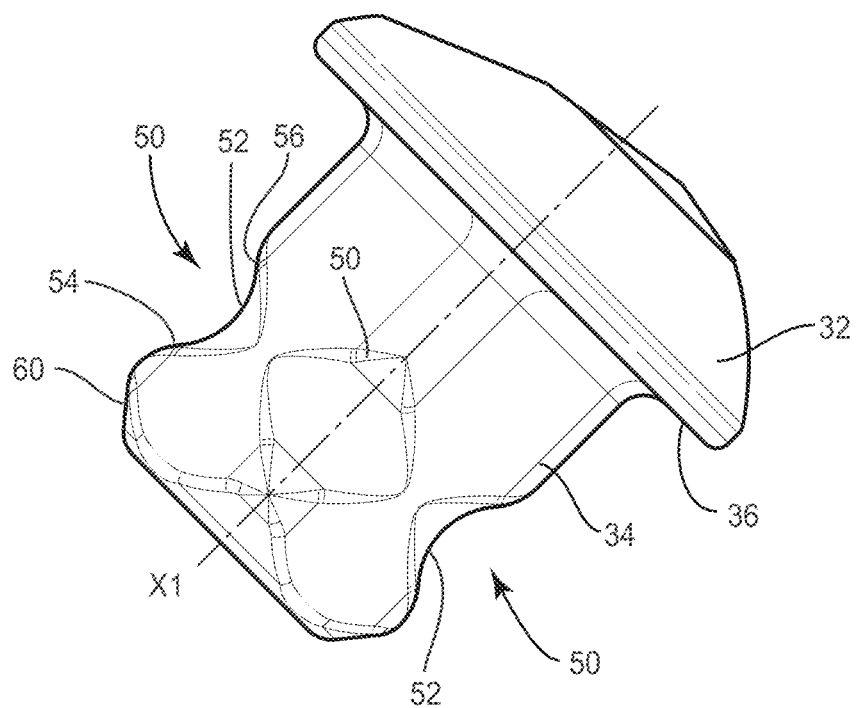
FIG. 4 is a break away side view of the components shown in FIG. 1.

Head 34 includes a plurality of peripheral capture elements, for example, divots 50. Divots 50 are configured for engagement with a moveable arm, for example, a cantilevered tang 120 of surgical driver 14, as described herein. Divots 50 each include a recess disposed at each edge 46, as shown in FIGS. 1, 2 and 4. Divots 50 are equidistantly spaced apart and disposed in relative alignment about perimeter P, shown in FIG. 4. In some embodiments, head 34 may include one or a plurality of capture elements for engagement with a moveable arm of surgical driver 14. For example, head 34 may include a single divot. In some embodiments, surgical driver 14 may include one or a plurality of moveable arms, as described herein, for engagement with head 34.

Divots 52 each include a surface that defines a ramp 54. Ramp 54 is oriented to decline from proximal end 40 to distal end 42, as shown in FIG. 4. During engagement of surgical driver 14 with bone screw 12, ramp 54 facilitates aligning and/or guiding a prong 122 of tang 120 into divot 50 to capture bone screw 12, as described herein. During disengagement of surgical driver 14 from bone screw 12, ramp 54 facilitates releasable engagement of tang 120 with head 34. For example, as tang 120 translates along ramp 54, the incline of ramp 54 overcomes the bias of tang 120 to facilitate release of tang 120 from divot 50.

Divots 52 each include a surface that defines a ramp 56. Ramp 56 is oriented to incline from proximal end 40 to distal end 42, as shown in FIG. 4. Ramp 56 facilitates limiting translation of prong 122 relative to head 34.

Head 34 includes an inclined surface, for example, a ramp 60 disposed at proximal end 40. Ramp 60 is oriented to incline from proximal end 40 to distal end 42, as shown in FIG. 4. Ramp 60 and ramp 54 are disposed in alignment along edge 46 and meet at an apex 62. During engagement of surgical driver 14 with bone screw 12, ramp 60 facilitates engagement with head 34 to capture bone screw 12, as described herein. For example, as tang 120 translates along ramp 60, the incline of ramp 60 and apex 62 is configured to overcome the bias of tang 120 causing tang 120 to splay from a shaft 100 of surgical driver 14. During disengagement of surgical driver 14 from bone screw 12, ramp 60 facilitates releasable engagement of tang 120 with head 34. For example, as tang 120 translates along ramp 54, the incline of ramp 54 and apex 62 overcomes the bias of tang 120 to facilitate release of tang 120 from head 34.

Figure 5:
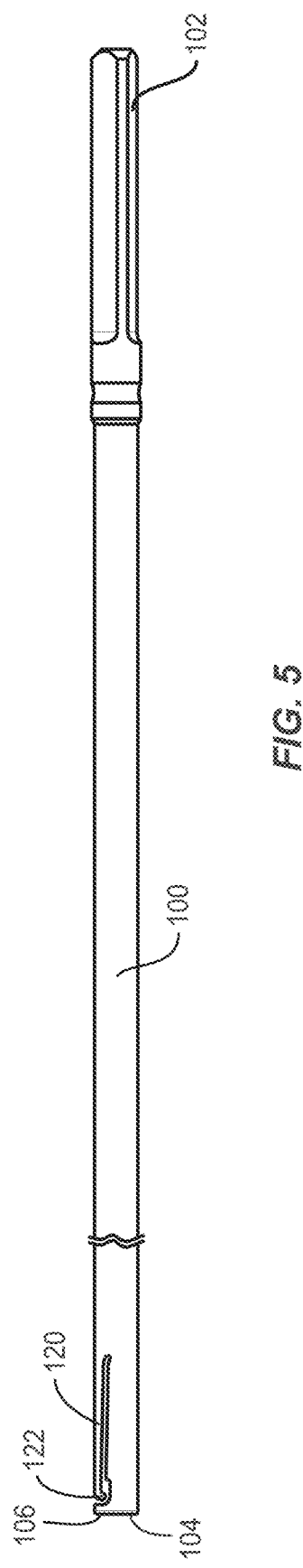
FIG. 5 is a side view of components of one embodiment of a surgical system in accordance with the principles of the present disclosure.
Figure 6:
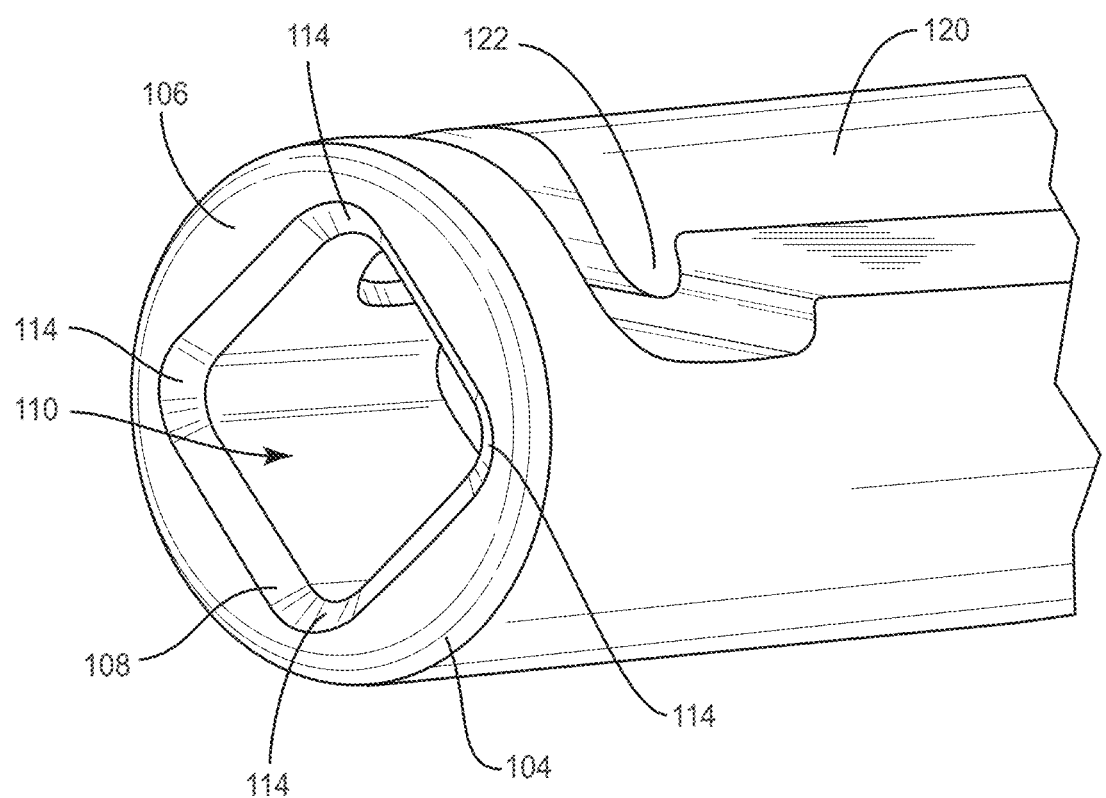
FIG. 6 is a break away perspective view of the components shown in FIG. 5.
Figure 7:
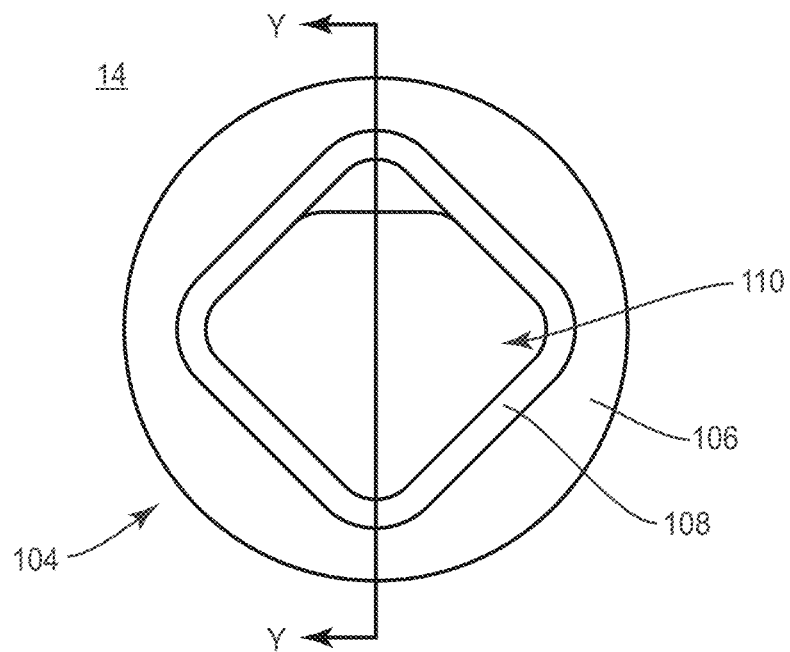
FIG. 7 is an axial view of the components shown in FIG. 5.
Figure 8:
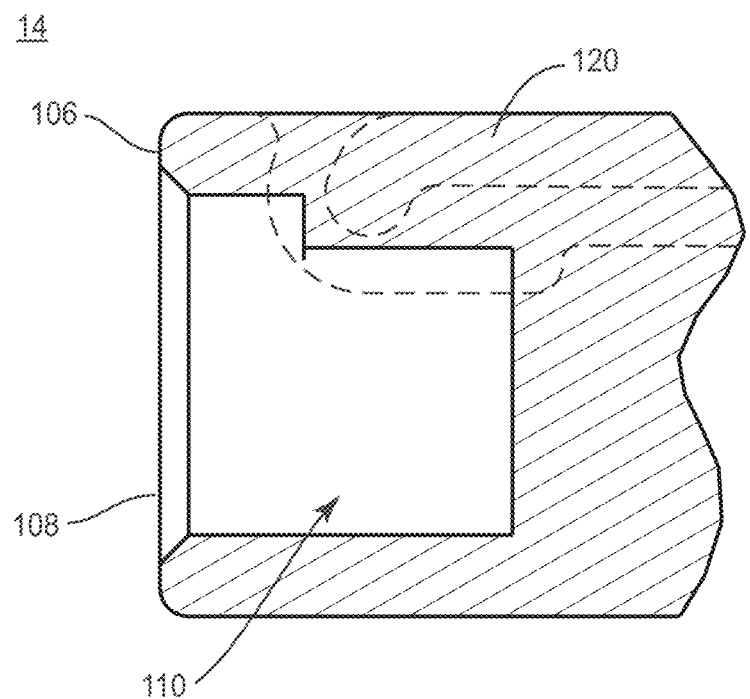
FIG. 8 is a break away cross section view along the lines Y-Y of the components shown in FIG. 7.

Shaft 100 extends between a proximal end 102 and a distal end 104, as shown in FIG. 5. Shaft 100 defines an axis X2. Proximal end 102 is configured for connection with an actuator such as a handle and/or powered drill to facilitate engagement of bone screw 12 with tissue. Distal end 104 includes a distal face 106 configured for engagement with proximal face 36, as shown in FIG. 5. Distal face 106 includes a surface 108 that defines an opening 110. Opening 110 is non-circular, for example, including a rectangular configuration such that opening 110 is configured for disposal of head 34 in a mating engagement. In some embodiments, opening 100 may have alternate cross section configurations, such as, for example, oval, oblong, triangular, square, polygonal, irregular, uniform, non-uniform, offset, staggered, and/or tapered. Surface 108 includes a beveled surface that is oriented to incline from distal face 106 towards proximal end 102, as shown in FIG. 6, to align and/or guide head 34 into opening 110. Opening 110 incudes corners 114 configured for alignment with edges 46 such that divot 50 is aligned for engagement with prong 122.

Figure 9:
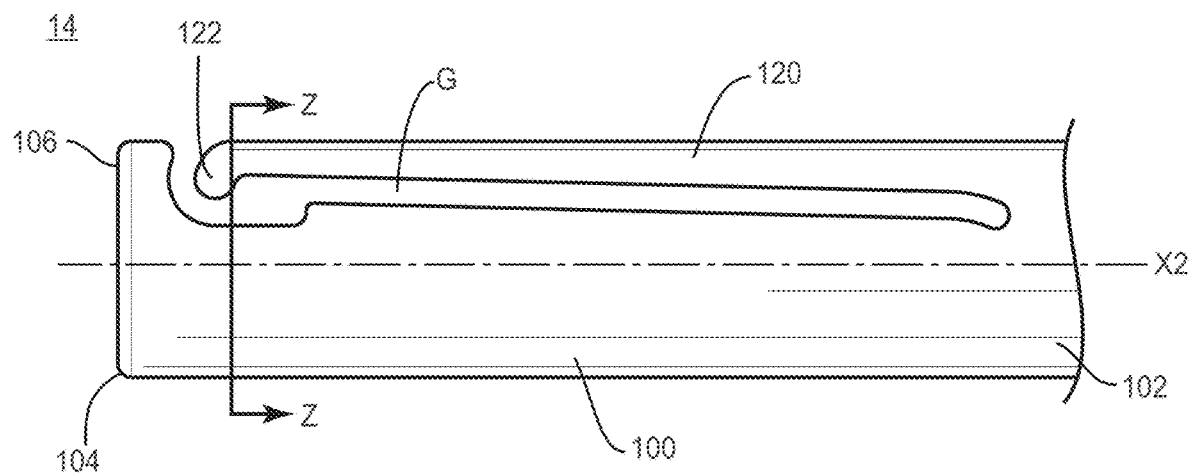
FIG. 9 is a break away side view of the components shown in FIG. 5.
Figure 10:
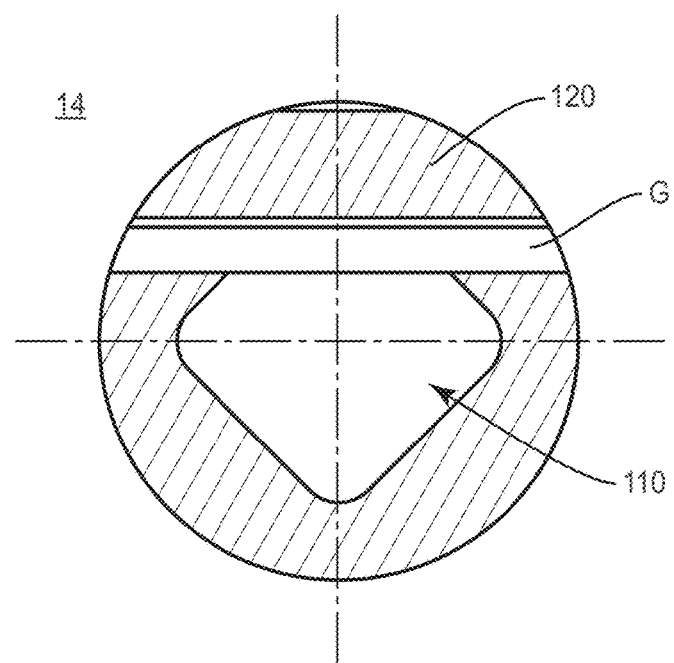
FIG. 10 is an axial cross section view along the lines Z-Z of the components shown in FIG. 9.

Tang 120 extends along shaft 100 parallel to axis X2, as shown in FIG. 9. Tang 120 extends such that a gap G is disposed between shaft 100 and tang 120 forming a living hinge such that tang 120 is rotatable relative to shaft 100. Gap G is disposed in communication with opening 110 to receive a portion of head 34, as shown in FIG. 11. Prong 122 is disposed at a distal end of tang 120. Prong 122 projects inward in a hook configuration such that prong 122 is oriented to capture bone screw 12. Tang 120 is rotatable relative to shaft 100 to orient prong 122 between a capture orientation and a release orientation. In the capture orientation, tang 120 is disposed parallel to axis X2 and prong 122 is disposed with divot 50. In the release orientation, tang 120 is rotated transverse to axis X2 to disengage prong 122 from divot 50, as described herein.

For example, surgical driver 14 is positioned relative to bone screw 12 such that head 34 is disposed adjacent to opening 110. Tang 120 is disposed parallel to axis X2. Head 34 is inserted into opening 110, in a direction shown by arrow A in FIG. 11. Surface 108 aligns and/or guides head 34 into opening 110 such that edges 46 are disposed with corners 114. The surface of ramp 60 engages prong 122. Prong 122 translates along ramp 60 towards apex 62. Translation of prong 122 along ramp 60 and over apex 62 overcomes the bias of tang 120 causing tang 120 to rotate and/or splay outward, in a direction shown by arrow B in FIG. 11. Prong 122 translates along ramp 54 into divot 50. The resilient bias of tang 120 causes tang 120 to rotate, in a direction shown by arrow C in FIG. 11, toward axis X2 to capture bone screw 12. As prong 122 translates into divot 50, distal face 106 translates into abutting engagement with proximal face 36 to resist/and or prevent further translation of surgical driver 14 relative to head 34. Ramp 56 resists and/or prevents further translation of prong 122.

To release bone screw 12, surgical driver 14 is manipulated, for example, translated in a direction shown by arrow D in FIG. 11. Prong 122 translates out of divot 50 and along ramp 54 towards apex 62. Translation of prong 122 over apex 62 overcomes the bias of tang 120 causing tang 120 to rotate and/or splay outward, in a direction shown by arrow B in FIG. 11. Prong 122 translates along ramp 60 to release bone screw 12 from surgical driver 14. The resilient bias of tang 120 causes tang 120 to rotate, in a direction shown by arrow C in FIG. 11, toward axis X2.

In assembly, operation and use, spinal implant system 10, similar to the systems and methods described herein, is employed with a surgical procedure, such as, for example, a laminoplasty treatment of a spine of a patient including vertebrae V, as shown in FIG. 12. The surgical system may also be employed with other surgical procedures, such as, for example, discectomy, laminotomy, laminectomy, nerve root retraction, foramenotomy, facetectomy, decompression, and spinal, nucleus or disc replacement. For example, a laminoplasty procedure is employed to alter one or more of the bony vertebral structures that surround and define the spinal canal. For example, vertebral levels V1, V2 and V3 of vertebrae V can be cut and/or weakened to open the canal and provide additional room for the spinal cord. In one embodiment, spinal implant system 10 stabilizes vertebral levels V1, V2 and V3 for proper healing.

In use, to treat the affected section of vertebrae V, a medical practitioner obtains access to a surgical site including vertebrae V in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure is performed for treating the spine disorder. Spinal implant system 10 is then employed to augment the surgical treatment. Spinal implant system 10 can be delivered or implanted as a pre-assembled device or can be assembled in situ. Spinal implant system 10 can be completely or partially revised, removed or replaced in situ. In some embodiments, one or all of the components of the implant system can be delivered to the surgical site via manual manipulation, image guided surgical navigation and/or a free hand technique.

An incision is made in the body of a patient and a cutting instrument (not shown) creates a surgical pathway for delivery of the components of spinal implant system 10 within the patient body to adjacent vertebral level V1.

Laminoplasty plate 300 is positioned in alignment for attachment with vertebral level V1 for attachment to tissue adjacent lamina L1 and L2. A pilot hole or the like is drilled with lamina L1 and plate 300 is disposed such that aperture 302 is positioned in alignment with the pilot hole in lamina L1 and aperture 304 is positioned in alignment with the pilot hole in lamina L2. Upon positioning of plate 300, bone screw 12 is utilized to attach plate 300 with tissue.

Surgical driver 14 is engaged with bone screw 12. Head 34 is inserted into opening 110 and surface 108 aligns and/or guides head 34 into opening 110 such that edges 46 are disposed with corners 114. The surface of ramp 60 engages prong 122 to translate prong 122 along ramp 60 towards apex 62. Tang 120 rotates and/or splays as prong 122 translates over apex 62. Prong 122 translates along ramp 54 into divot 50. The resilient bias of tang 120 causes tang 120 to rotate toward axis X2 to capture bone screw 12. As prong 122 translates into divot 50, distal face 106 translates into abutting engagement with proximal face 36 to resist/and or prevent further translation of surgical driver 14 relative to head 34. Ramp 56 resists and/or prevents further translation of prong 122. Bone screw 12 is engaged with tissue. Driver 12 is utilized to manipulate, fasten, drive, torque or insert shaft 16 with tissue.

Bone screw 12 is released by manipulating surgical driver 14. Prong 122 translates out of divot 50 and along ramp 54 towards apex 62. Translation of prong 122 over apex 62 causes tang 120 to rotate and/or splay to release bone screw 12 from surgical driver 14, as described herein.

Upon completion of a procedure, the surgical instruments and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
    a first member including a proximal end and an opposite distal end, the first member comprising a helical thread configured to penetrate tissue extending continuously from the proximal end to the distal end, the first member comprising a flute extending through the thread; and
    a second member including an abutment coupled to the proximal end and engageable with a surgical instrument and a head including at least one peripheral capture element engageable with a moveable arm of the surgical instrument, the head including a proximal surface and an opposite distal surface directly engaging a proximal face of the abutment, the proximal face extending 360 degrees about the head, the head being free of any openings or recesses extending into the proximal surface, wherein the moveable arm is rotatable relative to the surgical instrument for engagement with the second member between a capture orientation and a release orientation, wherein the head includes a rectangular cross section configuration, wherein the rectangular cross section configuration defines four corners of the head, the at least one capture element including a plurality of recesses, the recesses each extending into one of the corners, and wherein the recesses are spaced apart from the abutment.

2. A spinal implant as recited in claim 1, wherein the abutment includes a tapered distal surface.

3. A spinal implant as recited in claim 1, wherein the proximal face includes a stop for limiting translation of the surgical instrument relative to the second member, the stop extending 360 degrees about an outer surface of the head, the outer surface extending transverse to the proximal face.

4. A spinal implant as recited in claim 1, wherein the recesses are disposed in relative alignment about the second member.

5. A spinal implant as recited in claim 1, wherein the at least one capture element includes a plurality of divots being equidistantly spaced apart about the head.

6. A spinal implant as recited in claim 1, further comprising a laminoplasty plate connectable with the members.

7. A spinal implant as recited in claim 1, wherein the head includes a proximal end that includes the proximal surface and an opposite distal end that includes the distal surface, the recesses each including a first ramp that declines from the proximal end of the head to the distal end of the head and a second ramp that inclines from the proximal end of the head to the distal end of the head.

8. A spinal implant as recited in claim 1, wherein the head includes a proximal end that includes the proximal surface and an opposite distal end that includes the distal surface, the recesses each being positioned closer to the proximal end of the head than the distal end of the head.

9. A spinal implant as recited in claim 1, wherein the head includes a cavity extending into an outer surface of the head, the cavity being positioned between two of the recesses.

10. A spinal implant comprising:
a first member including a proximal end and an opposite blunt distal end, the first member comprising a helical thread configured to penetrate tissue extending continuously from the proximal end to the distal end, the first member comprising a flute extending through the thread; and
a second member including an abutment coupled to the proximal end and engageable with a surgical instrument and a head including at least one peripheral capture element engageable with a moveable arm of the surgical instrument, the head including a proximal surface and an opposite distal surface directly engaging a proximal face of the abutment, the proximal face extending 360 degrees about the head, the head being free of any openings or recesses extending into the proximal surface,
wherein the moveable arm is rotatable relative to the surgical instrument for engagement with the second member between a capture orientation and a release orientation,
wherein the head includes a rectangular cross section configuration,
wherein the rectangular cross section configuration defines four corners of the head, the at least one capture element including a plurality of recesses, the recesses each extending into one of the corners, and
wherein the head includes a proximal end that includes the proximal surface and an opposite distal end that includes the distal surface, the recesses each including a first ramp that declines from the proximal end of the head to the distal end of the head and a second ramp that inclines from the proximal end of the head to the distal end of the head.

11. A spinal implant as recited in claim 10, wherein the abutment includes a tapered distal surface.

12. A spinal implant as recited in claim 10, wherein the proximal face includes a stop for limiting translation of the surgical instrument relative to the second member, the stop extending 360 degrees about an outer surface of the head, the outer surface extending transverse to the proximal face.

13. A spinal implant as recited in claim 10, further comprising a laminoplasty plate connectable with the members.

14. A spinal implant comprising:
a first member including a proximal end and an opposite blunt distal end, the first member comprising a helical thread configured to penetrate tissue extending continuously from the proximal end to the distal end, the first member comprising a flute extending through the thread; and
a second member including an abutment coupled to the proximal end and engageable with a surgical instrument and a head including at least one peripheral capture element engageable with a moveable arm of the surgical instrument, the head including a proximal surface and an opposite distal surface directly engaging a proximal face of the abutment, the proximal face extending 360 degrees about the head, the head being free of any openings or recesses extending into the proximal surface,
wherein the moveable arm is rotatable relative to the surgical instrument for engagement with the second member between a capture orientation and a release orientation,
wherein the head includes a rectangular cross section configuration,
wherein the rectangular cross section configuration defines four corners of the head, the at least one capture element including a plurality of recesses, the recesses each extending into one of the corners, and
wherein the head includes a cavity extending into an outer surface of the head, the cavity being positioned between two of the recesses.

15. A spinal implant as recited in claim 14, wherein the abutment includes a tapered distal surface.

16. A spinal implant as recited in claim 14, wherein the proximal face includes a stop for limiting translation of the surgical instrument relative to the second member, the stop extending 360 degrees about an outer surface of the head, the outer surface extending transverse to the proximal face.

17. A spinal implant as recited in claim 14, further comprising a laminoplasty plate connectable with the members.

* * * * *